(12) United States Patent
Rai et al.

(10) Patent No.: US 8,179,270 B2
(45) Date of Patent: May 15, 2012

(54) METHODS AND SYSTEMS FOR PROVIDING SLEEP CONDITIONS

(75) Inventors: Deepti Dunichand Rai, Dorchester, MA (US); Steven F. Kalik, Arlington, MA (US)

(73) Assignee: Toyota Motor Engineering & Manufacturing North America, Inc., Ann Arbor, MI (US)

( * ) Notice: Subject to any disclaimer, the term of this patent is extended or adjusted under 35 U.S.C. 154(b) by 412 days.

(21) Appl. No.: 12/506,461

(22) Filed: Jul. 21, 2009

(65) Prior Publication Data

US 2011/0018720 A1 Jan. 27, 2011

(51) Int. Cl.
G08B 23/00 (2006.01)

(52) U.S. Cl. ........................................ 340/575; 600/300

(58) Field of Classification Search .................. 340/575, 340/573.1; 128/920; 600/300, 301
See application file for complete search history.

(56) References Cited

U.S. PATENT DOCUMENTS

| | | | |
|---|---|---|---|
| 4,228,806 A | 10/1980 | Lidow | |
| 5,928,133 A | 7/1999 | Halyak | |
| 7,118,530 B2 * | 10/2006 | Hursh et al. | 600/300 |
| 7,207,938 B2 * | 4/2007 | Hursh | 600/300 |
| 7,248,915 B2 | 7/2007 | Ronholm | |
| 7,956,756 B2 * | 6/2011 | Kubey et al. | 340/575 |
| 2002/0005784 A1 * | 1/2002 | Balkin et al. | 340/573.1 |
| 2006/0200008 A1 | 9/2006 | Moore-Ede | |
| 2007/0249952 A1 | 10/2007 | Rubin et al. | |
| 2008/0071150 A1 | 3/2008 | Miesel et al. | |
| 2010/0152546 A1 * | 6/2010 | Behan et al. | 600/301 |
| 2010/0332443 A1 * | 12/2010 | Gartenberg | 706/54 |

OTHER PUBLICATIONS

Infinitemonkeytheory, Child's Sleep Cycle Calculator, Dashboard Widgets, <http://www.apple.com/downloads/dashboard/calculate_convert/childssleepcyclecalculator.html>, Jul. 21, 2009.
Steven R. Hursch, Fatigue Models for Applied Research in Warfighting, Aviation, Space, and Environmental Medicine, 2004.

* cited by examiner

Primary Examiner — John A Tweel, Jr.
(74) Attorney, Agent, or Firm — Garrana Tran LLP; Andrea E. Tran (57) ABSTRACT

A method for monitoring a sleep condition with a sleep scheduler is disclosed wherein the method includes receiving a sleep parameter via an input receiver on the sleep scheduler. The method further includes associating the sleep parameter with an overall alertness and outputting a determined sleep condition based on the overall alertness. A system for providing a sleep condition is further disclosed therein the system comprising includes a display, an input receiver operable to receive a sleep parameter, and a processor in communication with the display. The processor may be operable to determine an overall alertness associated with the sleep parameter and wherein the processor is operable to output a determined sleep condition based on the overall alertness.

20 Claims, 4 Drawing Sheets

METHODS AND SYSTEMS FOR PROVIDING SLEEP CONDITIONS

TECHNICAL FIELD

The present disclosure relates generally to the field of monitoring sleep and wake conditions, and more specifically, to methods and systems for providing optimum sleep conditions.

BACKGROUND

For any task or occupation, sleep deprivation can result in the decline of alertness levels, thereby resulting in the degradation of work performance. To this end, sleeping may be considered an effective countermeasure to prevent decline in alertness levels. Two important factors related to sleeping include wake inertia and sleep inertia. Generally, wake inertia may be defined as the latency or time needed to begin sleeping while sleep inertia may refer to a post-awakening degradation of performance (i.e., "grogginess"). Furthermore, the positive effects of sleeping can depend on various factors such as the time of day, the amount of any sleep deprivation experienced, and the length of the nap. Therefore, as sleeping may provide significant improvements in alertness levels, determining the ideal sleep start time and sleep duration to afford minimum wake and sleep inertia may be important to maximizing the recovery effects of sleeping.

Furthermore, though sleep patterns may vary, it is generally accepted that individuals pass through various stages during sleep, called sleep stages. Typically, sleep may be categorized into either Rapid Eye Movement (REM) sleep or non-REM sleep. Non-REM sleep may be associated with four sleep stages, with sleep stages 1 and 2 corresponding to lighter sleep and sleep stages 3 and 4 corresponding to deeper sleep.

While a number of biological alarms that monitor sleep patterns of a user are available on the market, these alarms are primarily concerned with reducing the effects of sleep inertia associated with waking up from a night time sleep episode. Some products, for example, focus on scanning for a user's light stages of sleep (Stages 1 and 2) in the sleep cycle and waking up the user during near these moments at or near the user's scheduled wake-up time. In effect, these products attempt to reduce the sleep inertia associated with waking up from a deep stage of sleep. Notably, current products do not incorporate the influences of sleep debt and the time of day into their calculations for sleep inertia, though both factors may significantly affect sleep inertia. Furthermore, since current designs focus on night time sleep episodes, they do not take into account the wake inertia associated with day time naps where a person may have difficulty failing asleep.

Thus, a need exists for systems and methods for monitoring sleep conditions and providing optimum sleep conditions. Such systems and methods determine sleep conditions which may improve alertness such as by minimizing sleep inertia after a user awakens and minimizing wake inertia as a user prepares to fall asleep.

SUMMARY

The following presents a general summary of several aspects of the disclosure in order to provide a basic understanding of at least some aspects of the disclosure. This summary is not an extensive overview of the disclosure. It is not intended to identify key or critical elements of the disclosure or to delineate the scope of the claims. The following summary merely presents some concepts of the disclosure in a general form as a prelude to the more detailed description that follows.

One aspect of the disclosure provides for a method for monitoring a sleep condition with a sleep scheduler, wherein the method includes receiving a sleep parameter via an input receiver on the sleep scheduler. The method further includes associating the sleep parameter with an overall alertness and outputting a determined sleep condition based on the overall alertness.

Another aspect of the disclosure is a method for providing a sleep condition with a sleep scheduler, wherein the method includes receiving a sleep parameter. The method further includes determining an estimated alertness and an alertness requirement based on the sleep parameter and outputting a determined sleep condition based on an alertness difference between the estimated alertness and an alertness requirement.

A further aspect of the disclosure provides for a system to provide a sleep condition, the system includes a display and an input receiver operable to receive a sleep parameter. The system further includes a processor in communication with the display, wherein the processor is operable to determine an overall alertness associated with the sleep parameter and wherein the processor is operable to output a determined sleep condition based on the overall alertness.

Yet another aspect of the disclosure provides for a computer-readable medium having computer-executable instructions for performing a method of monitoring a sleep condition. The method includes receiving a sleep parameter via an input receiver. The method further includes associating the sleep parameter with an overall alertness and outputting a determined sleep condition based on the overall alertness.

Another aspect of the present disclosure provides for a computer-readable medium having computer-executable instructions for performing a method of providing a sleep condition with a sleep scheduler, wherein the method includes receiving a sleep parameter. The method further includes determining an estimated alertness and an alertness requirement based on the sleep parameter and outputting a determined sleep condition based on an alertness difference between the estimated alertness and an alertness requirement.

BRIEF DESCRIPTION OF THE DRAWINGS

For detailed understanding of the present disclosure, references should be made to the following detailed description of the several aspects, taken in conjunction with the accompanying drawings, in which like elements have been given like numerals and wherein.

DETAILED DESCRIPTION

Before the present systems, methods, and computer-readable media are described, it is to be understood that this disclosure is not limited to the particular systems, methods and media described, as such may vary. Also, the present disclosure is not limited in its application to the details of construction, arrangement or order of components and/or steps set forth in the following description or illustrated in the figures. Thus, the disclosure is capable of other aspects, embodiments or implementations or being carried out/practiced in various other ways.

One of ordinary skill in the art should understand that the terminology used herein is for the purpose of describing possible aspects, embodiments and/or implementations only, and is not intended to limit the scope of the present disclosure which will be limited only by the appended claims. Further, use of terms such as "including", "comprising", "having", "containing", "involving", "consisting", and variations thereof are meant to encompass the listed thereafter and equivalents thereof as well as additional items.

It must also be noted that as used herein and in the appended claims, the singular forms "a," "and," and "the" may include plural referents unless the context clearly dictates otherwise. Thus, for example, reference to "a device" refers to one or several devices and reference to "a method of monitoring" includes reference to equivalent steps and methods known to those skilled in the art, and so forth.

Figure 1:
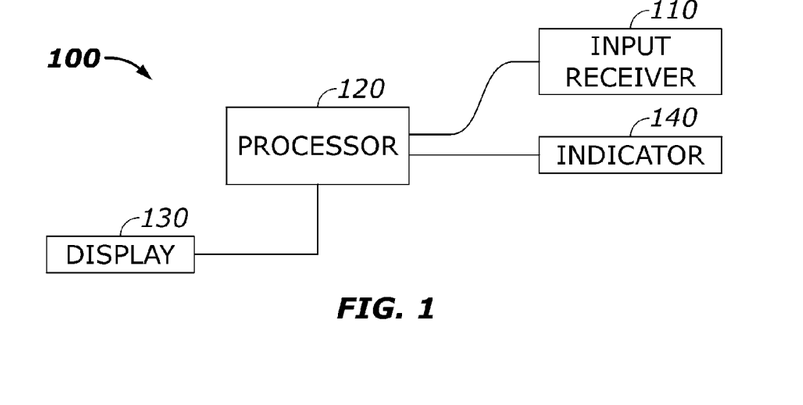
FIG. 1 provides a schematic illustrating a system for providing sleep conditions in accordance with one aspect of the present disclosure.

Moving now to FIG. 1, a general schematic is provided depicting a system, indicated generally at 100, for monitoring and/or providing sleep conditions. The system 100 may include any instrumentality or aggregate of instrumentalities operable to compute, classify, process, transmit, receive, retrieve, originate, store, display, detect, record, reproduce, handle, or utilize any form of information related to sleep and/or wake conditions of a user. Information in the form of data, signals, or the like, may be received by an input receiver 110 (to be described below) to be conveyed to a processor 120. The processor 120 may comprise a microprocessor, minicomputer, or any other suitable device, including combinations and/or a plurality thereof, for executing instructions related to the handling of the data from the input receiver 110. Based on parameters, instructions, algorithms, programs, or the like, the processor 120 may output information via a display 130 or an indicator 140 to notify a user, for example, of a particular sleep or wake condition.

Figure 2:
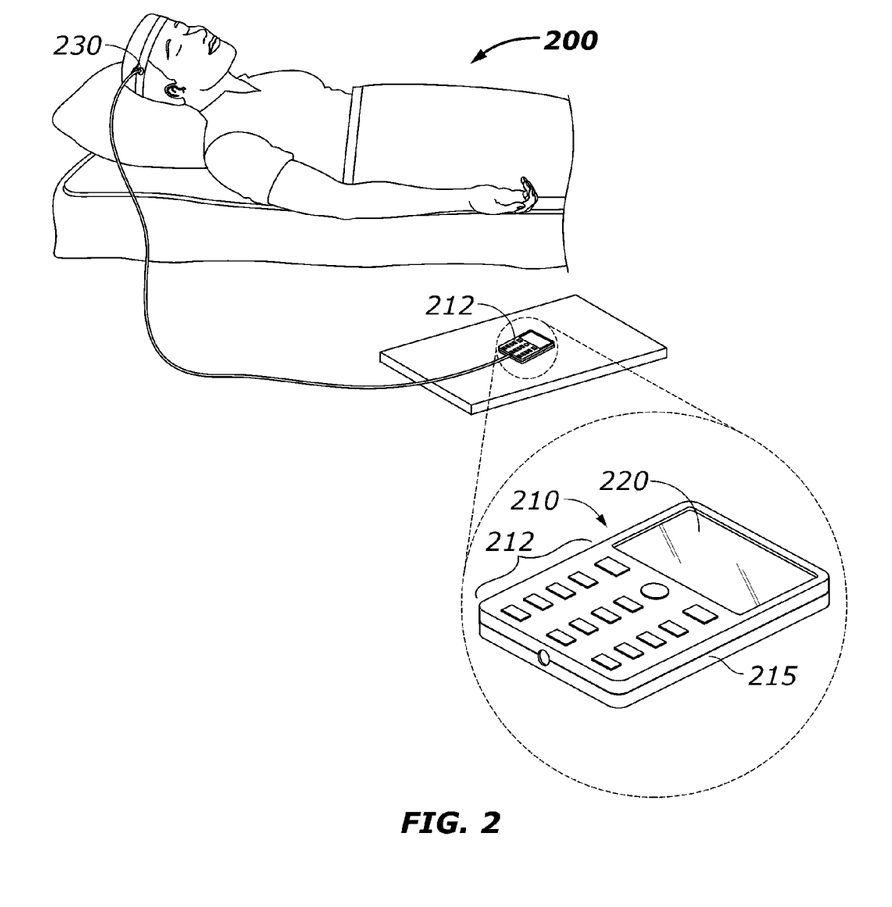
FIG. 2 provides a schematic illustrating a system for providing sleep conditions to a user in accordance with one aspect of the present disclosure.

Turning now to FIG. 2, is shown one possible implementation of a system for providing sleep or wake conditions. The system for monitoring and/or providing sleep conditions is shown as a sleep scheduler 210, as one example. The sleep scheduler 210 may be any electronic device disposed within a housing 215 or may be included on any electronic device. For example, the sleep scheduler 210 may be included as part of a personal digital assistant (PDA) or wristwatch.

The sleep scheduler 210 may include an input receiver 212 for receiving an input, from a user 200 in some implementations. Although the input receiver 212 is shown in FIG. 2 as a keypad, various forms of the input receiver 212 may be a keyboard, a button, a trackwheel, or other suitable means for a user to input or select information to be received by the sleep scheduler 210. According to another implementation, an input receiver 212 may comprise a sensor 230, such as an electrode, for example, operable to receive an input in the form of a signal. Such signals could include ElectroEncephalogram (EEG) signals, recorded with standard wet or dry EEG electrode methods. Those signals could be further filtered into particular frequency bands as are well known to those skilled in the art of recording and analyzing EEG activity. For example, the average power for signals in the delta band range (e.g., 0.5-4 Hz), which is typically the dominant EEG activity during deep sleep stages (Stage 3 and Stage 4 sleep) as measured over a window of time, are the existing definition of the value of the homeostatic component of the sleep intensity model. This homeostatic component is also referred to as the Sleep Debt. Various types of input or information to be received by the sleep scheduler 210 may further include data associated with the user's sleep and wake states or sleep parameters such as sleep start time, wake time, sleep duration, estimated alertness level, type of task, projected alertness requirement associated with a task or the like.

Input(s) received by the sleep scheduler 210 may be converted to signals to be handled by a processor of the sleep scheduler 210. Conventional analog or digital circuits may utilize such signals to estimate when a nap will be required for a user and when to awaken a user from the nap.

The sleep scheduler 210 may also include a display 220 such as a liquid crystal display (LCD) or the like. The display 220 may show information including a user's sleep and wake conditions such as the aforementioned data associated, either inputted by a user, sensed by a sensor, determined by the sleep scheduler 210, provided by another source (e.g., computer) or store of such data, or produced by other means.

Figure 3:
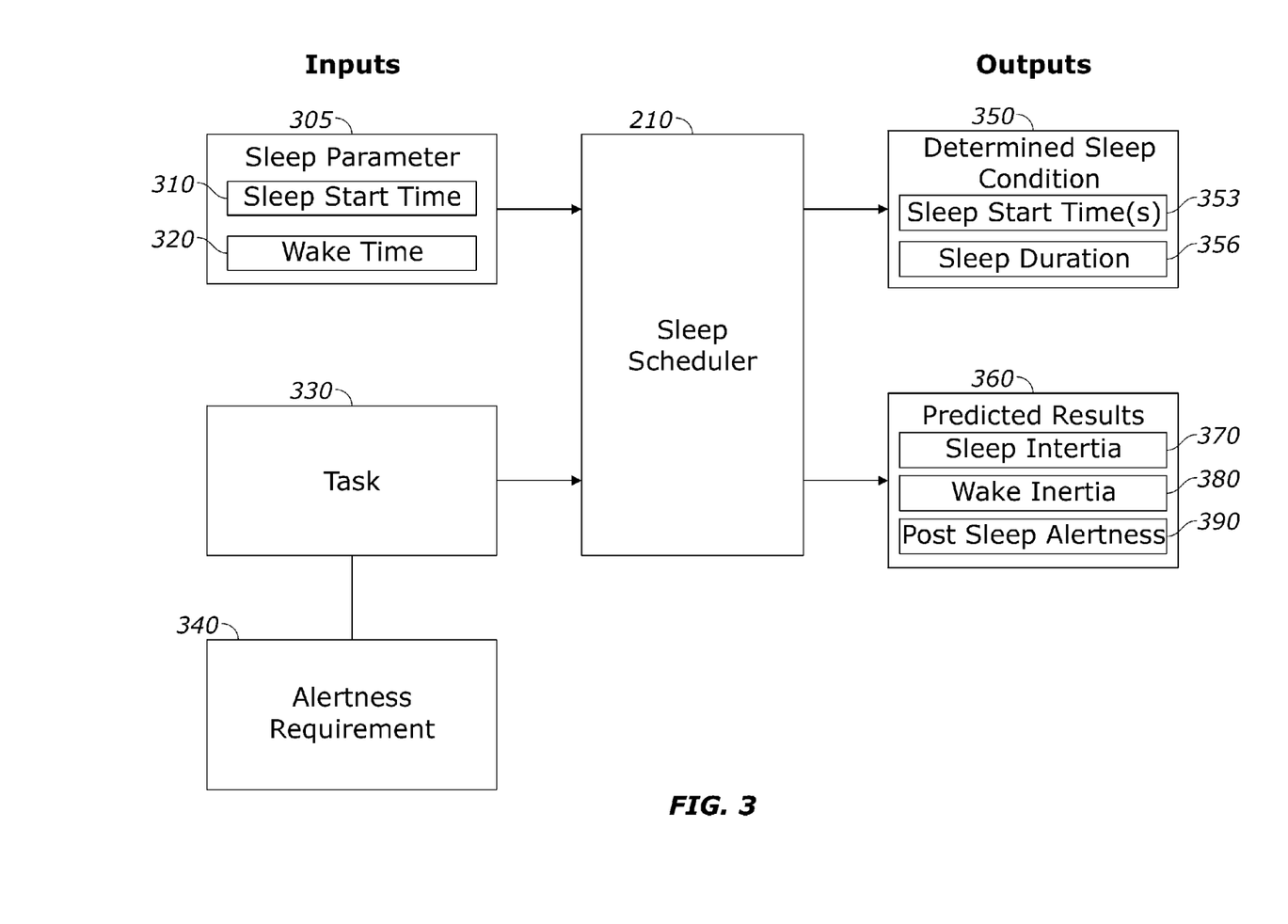
FIG. 3 provides illustrative inputs and outputs for the system of FIG. 1.

Moving now to FIG. 3, inputs such as sleep parameters 305 including sleep start time 310 and wake time 320 may be received or sensed by the sleep scheduler 210. The sleep start time 310 may correspond to the time a user falls asleep while wake time 320 corresponds to the time the user wakes up or a series of such events. For example, as user may input a sleep start time of 12:00 A.M. and a wake time of 8:00 A.M.

The task 330 may be another sleep parameter 305 which includes work or various activities, for example, that a user may perform throughout a period of time including, but not limited to, a day, week, or month. Such single or multiple tasks 330 may include driving, completing a document for work, exercising, or the like. Associated with each task 330 may be an alertness requirement 340, indicative of the alertness level required to adequately carry out a particular task 330. This input may be used to reflect the notion that certain tasks 330 may require higher alertness levels then other tasks 330, thereby presenting different alertness requirements 340 associated with those respective tasks 330. As one possible example, driving a vehicle may be associated with a higher alertness requirement 340 than inputting data in a spreadsheet. Although FIG. 3 depicts specific inputs and/or sleep parameters 305 such as sleep start time 310, wake time 320, task(s) 330, and alertness requirement 340, the present disclosure further contemplates any information related to sleep and wake states and/or conditions, such as desired sleep duration, may be within the scope of the present disclosure.

Continuing with FIG. 3, the sleep scheduler 210 may also produce outputs corresponding to the sleep start time 310, wake time 320, and task 330 inputs. In one implementation, the sleep scheduler 210 may determine and output at least one determined sleep condition 350 as well as at least one predicted result 360 that may occur from engaging in the determined sleep condition(s) 350. Determined sleep conditions 350 may include a proposed sleep start time 353 (i.e., suggested time of day to initiate sleep) and/or proposed sleep durations 356 (i.e., suggested length of sleep). Predicted results 360 may include the predicted sleep inertia 370, wake inertia 380, and/or post sleep alertness 390 that may result from engaging in sleep at the proposed sleep start times 353 and proposed sleep durations 356. Other implementations may include, but are not limited to, further inputs and/or outputs such as input data from a circadian rhythm oscillator or inputs from a homeostatic component estimator (based on recent sleep and wake history). Other implementations may further include, but are not limited to outputting a user's estimated alertness level. It should also be noted that as used herein, sleep can occur for any length of time including, but not limited to, typical sleep during the night (i.e., duration of continuous sleep exceeding 6 hrs) and/or taking a nap (i.e., short duration(s) of continuous sleep in increments of less than 1 hour).

Figure 4:
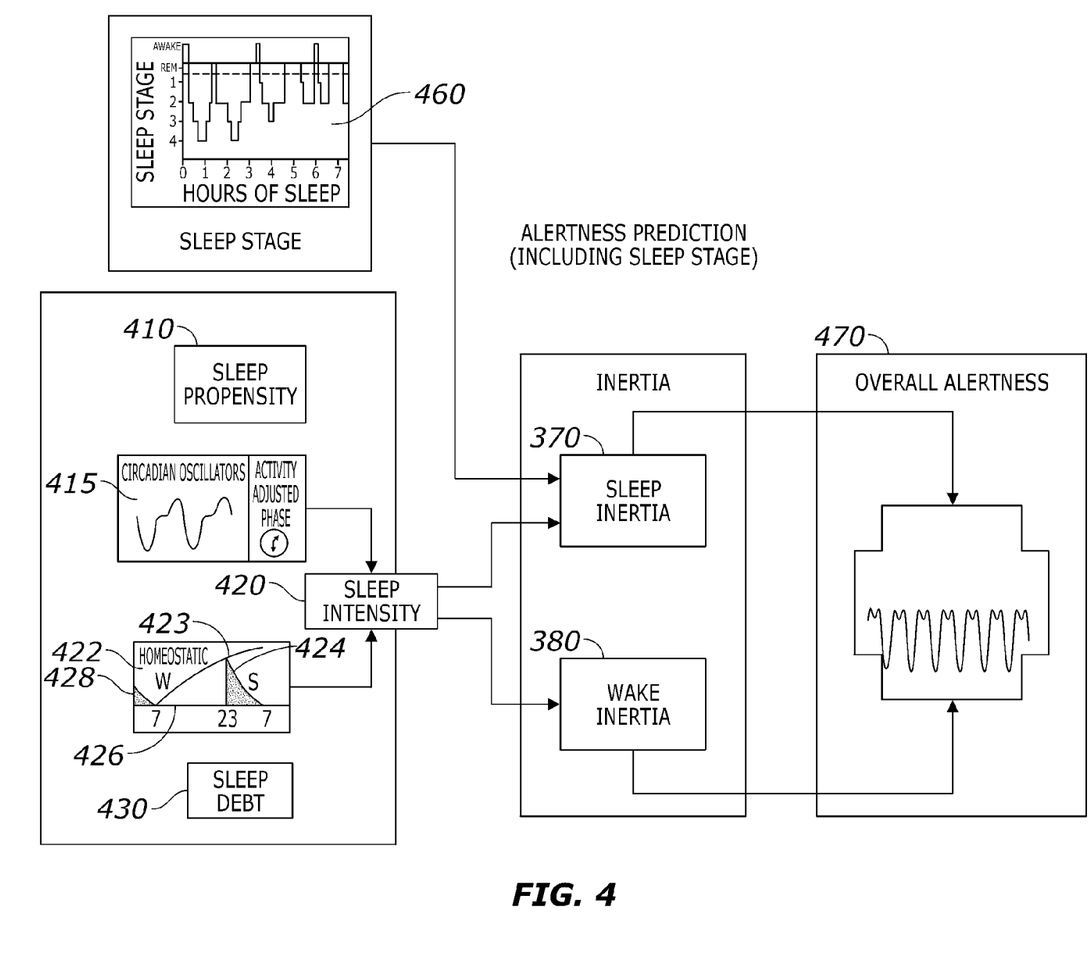
FIG. 4 illustrates sleep and wake conditions monitored by the system in FIG. 1.

Turning now to FIG. 4, a diagram is provided that represents a model for various sleep and wake states. As depicted, sleep intensity 420 may be considered a function of sleep propensity 410 and sleep debt 430. Both sleep propensity 410 and sleep debt 430 may be directly related to sleep intensity 420. All three variables may have a linear relationship according to the formula: Sleep Intensity=Sleep Debt−Sleep Propensity.

As used herein, sleep propensity 410 may correspond to the likelihood of a user failing asleep at a particular time of day, or as a function of the light dark cycle to which the user is exposed. This sleep propensity is distinguished from the sleep debt, in that the sleep debt is the probability of failing asleep based on past sleep and wake history (i.e., time since recent sleep and duration of that sleep), independent of the effects of light and dark cycle phase or overall time of day expressed as sleep propensity.

Exemplary sleep debt values may lie in a range approximately between 0 and 0.7, with a greater value corresponding to a higher sleep debt. Alternatively, exemplary sleep propensity values may lie in a range approximately between −0.2 and +0.2, where a negative value corresponds to high sleep propensity and a positive value corresponds to low sleep propensity. Hence, in the formula previously stated, high sleep debt and high sleep propensity will correspond to high sleep intensity. By way of illustration only, a high sleep debt value, such as 0.7, and a high sleep propensity value, such as −0.2, will result in a high sleep intensity value of 0.9.

Additionally, sleep propensity 410 may be measured by a circadian oscillator 415, which may simulate the circadian rhythm of an average person in a particular light/dark cycle, or of a specific person existing within or transitioning between the light/dark cycles of particular time zones. The circadian rhythm may refer to the fluctuations of physical and mental characteristics associated with a 24-hour day-night cycle. A person's sleep-wake cycle may be an example of a circadian rhythm and may in some instances be referred to as a person's "internal clock." To this end, the circadian oscillator may use the time of day, the amount of sunlight exposure, temperature and other factors to simulate a user's circadian rhythm and thereby determine the sleep propensity 410 of the user.

In one implementation, a circadian oscillator may be a device separate from the sleep scheduler, disclosed herein, including a processor that simulates the circadian rhythm of a user. In another implementation, the circadian oscillator may be a standalone program/simulation within the processor of the sleep scheduler. In any physical implementation, a circadian oscillator may receive input(s) from at least one sensor. Typical information received and/or recorded by the sensor(s) may include, but are not limited to, time of day, length of sunlight exposure or temperature. Information inputted by the sensor(s) may be utilized by the circadian oscillator to output the circadian rhythm which can be used to compute the sleep propensity and sleep intensity.

Sleep intensity 420, generally the inverse of alertness, may further be measured by the performance of a particular task. Sleep intensity may be the combination of influences of such as sleep debt (e.g., homeostatic effects) and sleep propensity (e.g., circadian effects) on overall performance of the task. For example, an employee may be rated by an employer with regard to the efficiency and quality by which the employee completes a particular task. Furthermore, this performance metric may fluctuate depending on how much rest the employee has had, the time of day, or the like. Indeed, an employee who has been severely deprived of sleep and is working late at night may experience low levels of efficiency and produce low work quality. In the situation just described, the sleep propensity 410 of the employee indicates an impact on their performance or need for sleep in the event they are working late at night. At the same time, the sleep debt 430, which will be further elucidated in the next paragraph, reflects another effect on performance or need for sleep, this time because of the separately mentioned sleep deprivation Sleep debt 430 may correspond to any sleep deficit a user possesses, or in other words, how much sleep a user's body is owed. Thus, sleep debt 430 may be based on a user's sleep parameters and/or conditions. In one implementation, a user's sleep debt may be modeled on an eight-hour sleep cycle where a user may sleep eight hours a day to maintain homeostasis within the body.

FIG. 4 may contemplate homeostasis with particular regard to the sleep-wake conditions of a user in order to calculate the user's sleep debt 430. In one implementation, a homeostatic model 422 may be used to simulate a user's sleep pressure 428 according to the amount of wake time 423 and sleep time 424 the user has experienced in their recent past. According to the model 422, sleep pressure 428 may be expressed with respect to the time of day 426. Under this framework, a sleep pressure of zero, for example, may indicate a level of homeostasis within the user. In addition, as illustrated by the homeostatic model 422, sleep pressure 428 may be a logarithmic function of wake time 423. Thus, the longer a person is awake, the further the person's body departs homeostasis. On the other hand, the sleep time 424 may be an exponential decay of sleep pressure 428 with respect to time 426 back to homeostasis. Thus, the rate at which sleep pressure 428 returns back to homeostasis during the sleep time 424 may be significantly quicker than increasing sleep pressure 428 during the wake time 423.

In one implementation, an Electroencephalograph (EEG) may be used to measure sleep debt 430. An EEG may be a device that measures and records electrical activity in the brain. To this end, an input receiver or sensor, such as an electrode, for example, may be attached to a person and also coupled to a computer to monitor brain activity. Furthermore, information obtained from EEGs may be used to identify different sleep stages of a user. As to be discussed in more detail below, data received from an EEG, indicative of sleep debt, may contribute to an overall alertness determination such as a calculated estimated alertness of a user.

In regards to sleep stages, sleep may be categorized into either Rapid Eye Movement (REM) sleep or non-REM sleep. Non-REM sleep may be associated with four sleep stages, with sleep stages 1 and 2 indicating a lighter sleep and sleep stages 3 and 4 indicating a deeper sleep. Furthermore, the sleep inertia 370 that may result from one waking up from a stage of deeper sleep may be larger than those of other stages associated with less deep sleep. Further still, some research suggests that waking up a user experiencing near REM sleep may result in near zero sleep inertia.

Sleep Intensity 420 may correspond to the rate at which sleep would replenish the energy of a user. Generally, sleep intensity may indicate the level of sleepiness, drowsiness or alertness of a user. Indeed, sleep intensity 420 may be dependent on sleep propensity 410 and sleep debt 430 by the aforementioned formula: Sleep Intensity=Sleep Debt−Sleep Propensity. Thus, high sleep intensity 420 may indicate a low level of alertness and high requirement for sleep while a low sleep intensity 420 may reflect the opposite, such as a high level of alertness and low requirement for sleep. While no standard units of measurement may exist for sleep propensity 410 and sleep debt 430, both components may be normalized and then weighted such that sleep intensity 420 may be weighted between 0 and 1.

In addition, sleep intensity 420 may be a factor in estimating a user's sleep inertia 370 and wake inertia 380. Wake inertia 380 may correspond to a period of time needed before sleeping can commence and may be a function of sleep intensity 420. On the other hand, sleep inertia 370 may correspond to a post-awakening degradation of performance or a general level of "grogginess." Furthermore, sleep inertia 370 may be a function of sleep intensity 420 as well as the sleep stage 460. In relation to sleep intensity 420, when sleep intensity 420 is measured at a high level, wake inertia 380 may be at a relatively low level while sleep inertia 370 can be at a relatively high level. In other words, a user who is significantly sleepy (i.e., at high sleep intensity 420) may require little time in failing asleep (i.e., at low wake inertia 380) but may suffer from low alertness levels immediately after waking up (i.e., large sleep inertia 370). In contrast, when sleep intensity 420 is low, sleep inertia 370 may be reduced but wake inertia 380 may be increased.

Finally, as depicted in FIG. 4 the overall alertness 470 of a user may be determined (e.g., simulated or estimated) based on quantities such as sleep propensity 410, sleep debt 430, sleep inertia 370, and/or wake inertia 380 of an individual. Overall alertness 470 may encompass various types of alertness including post sleep alertness, estimated alertness (EA), alertness requirement associated with a task, or the like. The estimated alertness (EA) of a user may be represented by the formula: $EA=C+(1-S)-Inertia$. Under this framework, EA represents estimated alertness, C represents sleep propensity 410, S represents sleep debt 430, and Inertia represents the combination of sleep inertia 370 and wake inertia 380. As previously mentioned, both inertia components may be estimated using the sleep intensity 420. Thus, the sleep scheduler may take into account sleep intensity 420, sleep inertia 370, and/or wake inertia 380.

In one implementation, the sleep scheduler may determine the optimum window of sleep intensity 420 and provide options for sleep start time and sleep durations for which the sleep inertia 370 and wake inertia 380 can be satisfactorily low. Providing such information may enable a user to select sleep start times and durations that maximize recovery effects (i.e., improvement in a user's alertness) subject to the user's schedule, preferences, and/or any other constraints that the user may have. Moreover, a tradeoff may exist between sleep duration and any improvements in estimated alertness. For example, a longer sleep may prove more beneficial if the sleep inertia 370 can be kept low when compared to a shorter sleep. Sleeping during certain times of the day may also affect recoveries in alertness. Therefore, in order to simplify decisions as to sleep timing for the user, the user may be provided with an option of choosing from suggestions given by the sleep scheduler regarding sleep start time and sleep duration. These suggestions, as determined by the user, may be based on the shortest sleep possible that would provide a benefit in alertness, or in terms of the maximum improvement in alertness that could be gained from a sleep. For example, if a user maintains a strict schedule and cannot afford long periods of sleep, the user may select the sleep scheduler to choose the shortest sleep durations or naps. The sleep scheduler may then output or display the corresponding sleep times at which it may be most efficient to sleep.

In another implementation, EA determined from the above formula may be compared to an alertness requirement (AR) determined by the sleep scheduler 210. A user's overall alertness 470 may encompass EA, AR or a comparison, such as the difference or alertness difference, between an EA and AR for a particular task. In addition, overall alertness 470 may be attributed to factors such as sleep debt 430, circadian oscillators 415, sleep stage 460, or the like. In turn, sleep parameters such as sleep start time and sleep duration(s) may yield predicted results 360 (e.g., sleep inertia 370 and wake inertia 380) which may also affect EA.

As previously mentioned in FIG. 3, the sleep scheduler 210 may receive at least one task 330 corresponding to an alertness requirement (AR) 340. AR for a particular task may be obtained from a database stored in the memory of sleep scheduler. The database may contain the alertness requirements, obtained experimentally or through other known means, for all basic types of tasks (e.g., driving, operating heavy machinery, reading, etc.). If a particular task is not present in the database, the user will be requested to input his/her subjective feeling of the level of risk (e.g., 1 for low risk; 10 for high risk) associated with an error in performing the task. Possible levels of risk may include high, medium, low, or the like. The risk estimate inputted by a user may be utilized to estimate (e.g., linear function, non-linear function) the AR for the task. In the event of a high risk task, the high level of risk may be associated with a high AR. Conversely, low risk may be associated with a low AR. An exemplary alertness scale may range from 0 to 1 where 0 indicates low alertness and 1 indicates high alertness. Depending upon the risk associated with occurrence of error while performing a particular task, another example of an alertness scale may indicate a range of greater than or equal to 0.4 for a low AR, greater than or equal to 0.6 for a medium AR, and greater than or equal to 0.8 for a high AR. It is also understood that various other methods may be employed to estimate the AR for a particular task.

In the case whereby AR exceeds EA, the sleep scheduler 210 may output an optimum window of sleep intensity and provide options for optimum sleep condition(s) such as sleep start time(s) and sleep duration(s).

Optionally, the user may also choose to manually input the desired sleep time or the sleep duration into the sleep scheduler 210. For example, if a user inputs a desired sleep time, the sleep scheduler 210 may then provide the corresponding sleep duration(s) that may result in maximum improvements in alertness. Furthermore, the sleep scheduler 210 may alert the user if it deems that a period of sleep during a particular time of day would not provide useful benefits. Such a situation may arise if the sleep or wake inertia is at a relatively high level. On the other hand, a user may also have the ability to input a desired sleep duration for which the sleep scheduler 210 may provide corresponding sleep and/or wake times for the sleep duration. Moreover, if an individual inputs a desired wake time, the sleep scheduler may propose an optimum wake up time, which may be more beneficial than that inputted by the user.

While FIG. 4 has been discussed with reference to a linear relationship between sleep intensity 420, sleep propensity 410, and sleep debt 430, it should be understood that the present disclosure is not limited to such a relationship. Indeed, various other types of relationships among sleep propensity 410, sleep debt 430, and sleep intensity 420 are also contemplated. Moreover, sleep inertia 370 and wake inertia 380 may be modeled as linear and/or nonlinear functions of sleep intensity 420. In addition, FIG. 4 illustrates only one model detailing the calculation of sleep debt 430. As such, various other methods of calculating sleep debt 430 (e.g., different curves for the wake time and sleep time on the homeostatic model 422) are also included within the present disclosure.

Figure 5:
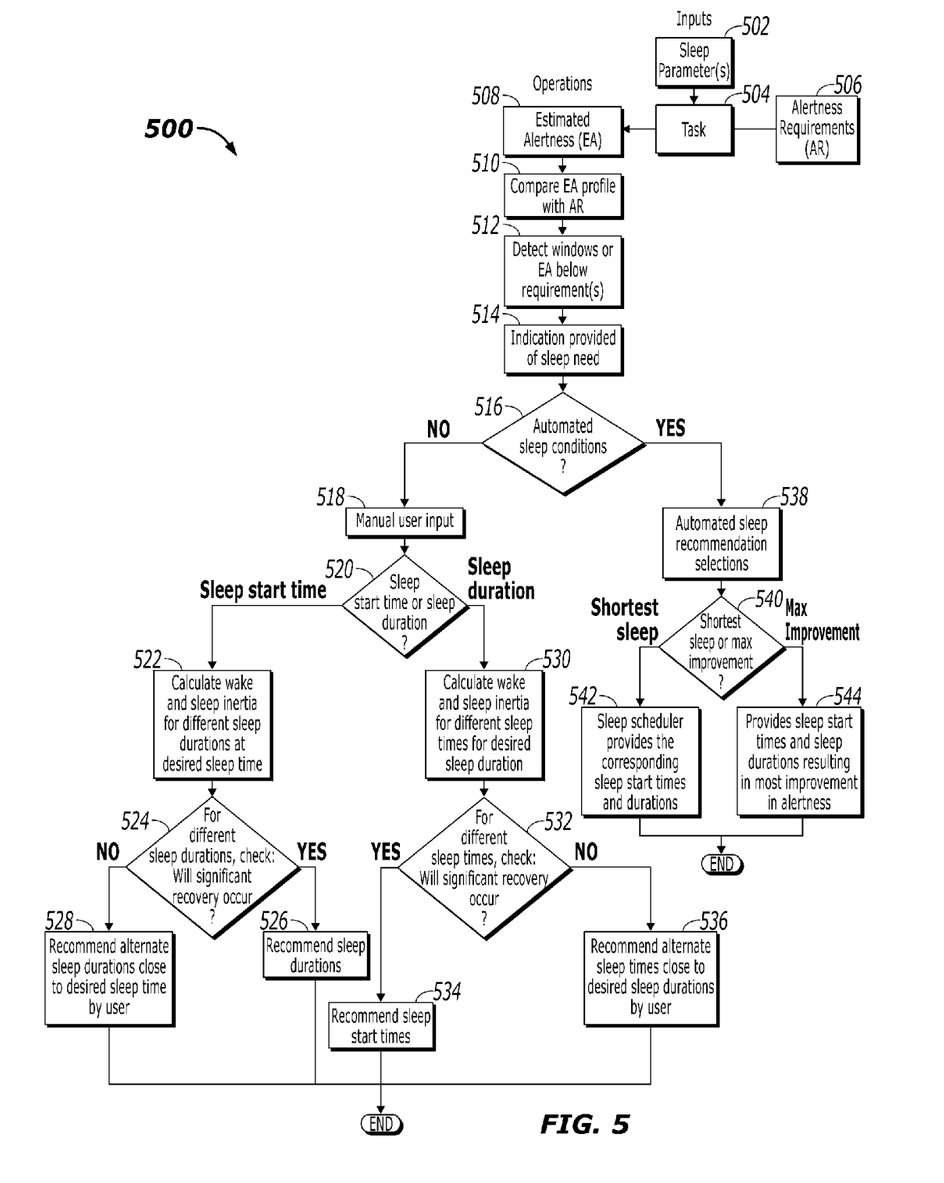
FIG. 5 provides a flow diagram of a method for providing information regarding sleep conditions in accordance with one aspect of the present disclosure.

Moving now to FIG. 5, a flow diagram is provided illustrating a method, indicated generally at 500, for monitoring and providing sleep conditions, in accordance with one aspect of the present disclosure. The method 500 may begin in step 502 when a sleep parameter is received by an input receiver of the sleep scheduler. The sleep parameter may include a sleep start time, such as the time a user went to bed the previous night, and the wake time at which the user awoke. Moreover, the sleep parameter may include similar information regarding any number of previous days of the user's sleep schedule. Next, at least one task may be inputted into the sleep scheduler in step 504. The task(s) may include activities that a user may be scheduled to perform throughout any specified period of time or during previous increments of time, including days and weeks. In other implementations, at least one task may be automatically inputted from a calendar or any other type of organizer that is already synchronized with the sleep scheduler.

The tasks 504 may also have associated alertness requirements 506, i.e., certain tasks may have specific alertness requirements that should be met in order to perform those tasks. For example, driving a vehicle a certain distance may have a different alertness requirement than operating heavy machinery.

In step 508, the sleep scheduler may simulate or determine the estimated alertness (EA) of the user. To this end, FIG. 4 has been previously discussed with respect to how the estimated alertness of a user may be estimated and predicted. Subsequently, in step 510, the sleep scheduler may compare a user's estimated alertness with alertness requirements associated with the user's task(s). For example, for a given period of time, the predicted fluctuations in the alertness requirements may be checked against the tasks that a user must perform. Thus, in step 512, the sleep scheduler may determine any window(s) of time where a user's estimated alertness may fall below an alertness requirement. Once the sleep scheduler detects such a window, the sleep scheduler may notify a user of a determined sleep condition, such as determined sleep duration or determined wake up time, needed to improve a user's estimated alertness in step 514. Sleep conditions such as optimum sleep duration, optimum sleep start time and optimum wake time may correspond to conditions of varying sleep/wake inertia and post-sleep alertness. For example, when the sleep scheduler determines an optimum sleep start time, the start time is based on one which is characterized by relatively low wake inertia, relatively high sleep intensity, and low overall alertness. Alternatively, an optimum wake time may correspond to a wake up time characterized by relatively low sleep inertia, lowered sleep intensity, and high post-sleep alertness.

The sleep scheduler may provide any suitable indicator of the optimum wake condition. For example, in the event that an optimum sleep duration is determined, an indicator such as digital data shown on the display of the sleep scheduler may suffice to alert a user of a need for sleep, particularly at a determined sleep start time. In another implementation, an indicator of an optimum wake time may be in the form digital data shown on the display or an alarm, buzzer, vibrator, other suitable indicator to wake a user from a period of sleep.

In step 516, the user may determine whether to have the sleep scheduler automatically provide automated sleep conditions to the user. Sleep conditions, such as the aforementioned determined sleep conditions, may include recommendation(s) as a sleep start time and/or duration for the sleep. To this end, the sleep scheduler may include an option that a user may set to either provide automated suggestions for sleep conditions or to allow for manual user input.

If the user elects for manual input in step 518, the user may have a choice for selecting either the desired sleep time or sleep length in step 520. If the user decides to select a desired sleep time, the sleep scheduler may then calculate the wake and sleep inertia for different experimental sleep durations at the desired sleep time in step 522. In step 524, for each experimental sleep duration, the sleep scheduler may then check if a significant recovery or improvement in alertness will occur as a result of the sleep. If such experimental sleep duration(s) exist for the desired sleep time, the sleep scheduler will recommend those sleep duration(s) in step 526. Otherwise, in step 528, the sleep scheduler may make recommendations of alternate sleep start times and their corresponding sleep lengths. In the event that there is no corresponding sleep durations that will result in significant recovery for a particular user inputted sleep start time, the sleep scheduler will recommend the user to change his/her desired sleep start time. To assist the user, the sleep scheduler will recommend alternate sleep times and their corresponding sleep lengths which will result in significant recovery.

In an implementation, the sleep scheduler may recommend alternate sleep times and their corresponding sleep lengths prioritized in terms of sleep start time closest (e.g., before or after) to the user's desired sleep time. For example, if the user enters the sleep start time as 2:00 PM, the sleep scheduler will compute all possible sleep lengths for the desired sleep time of 2:00 PM that will result in significant recovery. If no sleep episode of any length at 2:00 PM will result in significant recovery, the user will be notified of the same. In other words, the user will be notified that 2:00 PM is not a good sleep start time.

The sleep scheduler may automatically compute alternate sleep start time(s) and their corresponding sleep lengths for which significant recovery will occur. It may then provide the user with the alternate sleep start time(s) and their corresponding sleep lengths. In one possible implementation, the first choice to be displayed may be the one that is closest to the desired sleep time and results in maximum recovery. In the above example, assuming the sleep scheduler computes and estimates three alternative sleep start times that will result in significant recovery, the order in which the choices may be displayed to the user may be 2:30 PM, 1:00 PM, and 3:30 PM, for example. In another implementation, in the event that two estimated sleep start times have the same proximity to a desired sleep start time, whichever sleep start time results in greater recovery, as computed by the sleep scheduler, may be displayed as the first choice to the user. It should be understood that the present disclosure contemplates displaying an estimate sleep start time and/or sleep length in any suitable order.

If, on the other hand, the user chooses to manually input the desired sleep duration in step 520, the sleep scheduler may then calculate the sleep and wake inertia corresponding to various experimental sleep times for the desired sleep duration in step 530. Then, in step 532, for the different experimental sleep times, the sleep scheduler may determine if a significant recovery or improvement in the alertness of the user will result from the sleep. If so, the sleep scheduler may provide the corresponding sleep times in step 534. If not, in step 536, the sleep scheduler may recommend alternate sleep duration(s) and their corresponding sleep start times close to the desired sleep duration inputted by the user.

Turning back now to step 516, the user may also select the sleep scheduler to provide automated sleep-timing suggestions in step 538. In step 540, the user may then determine whether to have the sleep scheduler provide sleep times and sleep durations based on the shortest sleep or the greatest improvement in overall alertness. If the user wishes to select the shortest sleep in step 542, the sleep scheduler may provide the corresponding sleep times and sleep durations based on the shortest sleep. Otherwise, in step 544, the sleep scheduler may display sleep start time(s) and sleep durations that would result in the most improvement in overall alertness.

Thus, the present disclosure may provide methods and systems by which a sleep scheduler may notify the user of a need for sleep and propose suggested sleep start times, wake times, sleep durations or the like. The suggested sleep start times, wake times and/or sleep durations may be calculated as to minimize sleep inertia and wake inertia so as to enable the user to gain maximum recovery in the user's overall alertness level.

Furthermore, methods of the present disclosure, detailed description and claims may be presented in terms of logic, software or software implemented aspects typically encoded on a variety of media or medium including, but not limited to, computer-readable medium/media, machine-readable medium/media, program storage medium/media or computer program product. Such media, having computer-executable instructions, may be handled, read, sensed and/or interpreted by a computer. Generally, computer-executable instructions, such as program modules, may include routines, programs, objects, components, data structures, and the like, which perform particular tasks, carry out particular methods or implement particular abstract data types. Those skilled in the art will appreciate that such media may take various forms such as cards, tapes, magnetic disks (e.g., floppy disk or hard drive) and optical disks (e.g., compact disk read only memory ("CD-ROM") or digital versatile disc ("DVD")). It should be understood that the given implementations are illustrative only and shall not limit the present disclosure.

Although the present disclosure has been described with reference to particular examples, embodiments and/or implementations, those skilled in the art will recognize that modifications and variations may be made without departing from the spirit and scope of the claimed subject matter. Such changes in form and detail, including use of equivalent functional and/or structural substitutes for elements described herein, fall within the scope of the appended claims and are intended to be covered by this disclosure.

What is claimed is:

1. A method for monitoring a sleep condition with a sleep scheduler, the method comprising:
   receiving a sleep parameter via an input receiver on the sleep scheduler, wherein the sleep parameter comprises at least one task;
   associating the sleep parameter with an alertness requirement (AR);
   comparing an estimated alertness (EA) to the alertness requirement associated with the sleep parameter; and
   outputting a determined sleep condition when the AR exceeds the EA.

2. The method of claim 1, wherein the determined sleep condition comprises a determined sleep start time, a determined wake time, a determined sleep duration, or a combination thereof.

3. The method of claim 1, wherein the sleep parameter comprises an inputted sleep start time, an inputted wake time, an inputted sleep duration, or a combination thereof.

4. The method of claim 1 further comprising determining wake inertia and sleep inertia, the wake inertia and sleep inertia associated with an inputted sleep duration based on an inputted sleep start time.

5. The method of claim 1, wherein an overall alertness comprises an estimated alertness based on the sleep parameter, a required alertness associated with at least one task, or an alertness difference between the estimated alertness and the required alertness.

6. The method of claim 1, wherein the estimated alertness (EA) of a user is represented by: $EA=C+(1-S)$-Inertia, wherein C represents sleep propensity and S represents sleep debt.

7. A method for providing a sleep condition with a sleep scheduler, the method comprising:
   receiving a sleep parameter via an input receiver on the sleep scheduler;
   determining an alertness requirement (AR) based on the sleep parameter; and
   outputting a determined sleep condition based on an alertness difference between an estimated alertness of a user and the AR.

8. The method of claim 7, wherein the determined sleep condition comprises a determined sleep start time, a determined wake time, a determined sleep duration, or a combination thereof.

9. The method of claim 7, wherein the sleep parameter comprises an inputted sleep start time, an inputted wake time, an inputted sleep duration, or a combination thereof.

10. The method of claim 7 further comprising determining wake inertia and sleep inertia, the wake inertia and sleep inertia associated with an inputted sleep duration based on an inputted sleep start time.

11. The method of claim 7 further comprising recommending an optimum sleep duration in response to an inputted sleep start time.

12. The method of claim 7 further comprising recommending an optimum sleep start time in response to an inputted sleep duration.

13. The method of claim 7, further comprising:
   outputting a determined sleep condition when the alertness requirement exceeds the estimated alertness.

14. A system for providing a sleep condition, the system comprising:
   a display;
   an input receiver operable to receive a sleep parameter; and
   a processor in communication with the display, wherein the processor is operable to determine an alertness requirement (AR) associated with the sleep parameter and wherein the processor is operable to output a determined sleep condition when the AR exceeds an estimated alertness of a user.

15. The system of claim 14 further comprising:
   an indicator coupled to the processor, wherein the indicator is operable to notify a user of a determined wake time or a determined sleep duration.

16. The system of claim 15, wherein the indicator is selected from the group consisting of an alarm, a buzzer, a vibrator, or a combination thereof.

17. The system of claim 14, wherein the determined sleep condition comprises an determined sleep start time, a determined wake time, a determined sleep duration, or a combination thereof.

18. The system of claim 14, wherein the sleep parameter comprises an inputted sleep start time, an inputted wake time, an inputted sleep duration, or a combination thereof.

19. The system of claim 14, wherein the overall alertness comprises an estimated alertness based on the sleep parameter, a required alertness associated with at least one task, or an alertness difference between the estimated alertness and the required alertness.

20. The system of claim 14, wherein the determined sleep condition is outputted when an alertness requirement exceeds an estimated alertness.

* * * * *